United States Patent [19]
Vincentz et al.

[11] Patent Number: 5,569,833
[45] Date of Patent: Oct. 29, 1996

[54] METHOD FOR ENHANCING THE EARLINESS OF A PLANT AND/OR LOWERING THE CONTENT OF NITRATES STORED IN THE PLANT

[75] Inventors: Michel Vincentz, Paris; Francois Dorlhac, Meudon; Yves Chupeau, Richebourg; Jean-Franois Morot-Gaudry, Gif-sur-Yvette; Michel Caboche, Maurepas, all of France

[73] Assignee: Institut National de la Recherche Agronomique, Paris, France

[21] Appl. No.: 295,882

[22] PCT Filed: Mar. 5, 1993

[86] PCT No.: PCT/FR93/00222

§ 371 Date: Dec. 6, 1994

§ 102(e) Date: Dec. 6, 1994

[87] PCT Pub. No.: WO93/18154

PCT Pub. Date: Sep. 16, 1993

[30] Foreign Application Priority Data

Mar. 5, 1992 [FR] France ................................. 92 02658

[51] Int. Cl.$^6$ ................ A01H 5/00; C12N 15/53; C12N 15/84; C12N 15/29
[52] U.S. Cl. .................... 800/205; 800/DIG. 13; 800/DIG. 16; 800/DIG. 43; 800/DIG. 46; 435/69.1; 435/70.1; 435/172.3; 435/191; 435/320.1
[58] Field of Search ............... 435/69.1, 70.1, 435/172.3, 191, 320.1; 800/205, DIG. 13, 16, 43, 46

[56] References Cited

FOREIGN PATENT DOCUMENTS

| | | | |
|---|---|---|---|
| 0227909 | 7/1987 | European Pat. Off. | ........ C12N 15/00 |
| 0283338 | 9/1988 | European Pat. Off. | ........ C12N 15/00 |
| 0303780 | 2/1989 | European Pat. Off. | ........ C12N 15/00 |
| 9104325 | 4/1991 | WIPO | .............................. C12N 9/02 |

OTHER PUBLICATIONS

Plant Molecular Biology, vol. 18, Jan. 1992, Dordrecht, The Netherlands, pp. 363–375, Dorbe, M–F, et al. 'The tomato nia gene complements a Nicotina plumbaginifolia nitrate reductase deficient mutant and is properly regulated', see pages 371, left–hand column, paragraph 1.

The Plant Journal, vol. 1, No. 2, Sep. 1991, pp. 267–274, Nussaume, L., et al. 'Constitutive nitrate reductase: a dominant conditional marker for plant genetics' see p. 268–p. 269.

EMBO Journal, vol. 10, No. 5, 1991, Eynsham, Oxford GB, pp. 1027–1035; Vincentz, M. et al; "Constitutive expression of nitrate reductase allows normal growth and development of Nicotiana plumbaginifolia plants".

*Primary Examiner*—David T. Fox
*Attorney, Agent, or Firm*—Christie, Parker & Hale, LLP

[57] ABSTRACT

A method for enhancing plant precocity and/or reducing stored nitrate content of a plant, wherein an over-expression of nitrate reductase is induced in the plant so as to induce an over-expression of nitrate reductase activity therein.

12 Claims, 6 Drawing Sheets

```
GAGCTCGTT CCCAAACAGA ACAAGAAAAT CAAATCTCGG AGAGAGAGAG AGAGAAATAT    59

TTTGAGAGAG AAATACAGAA AATCTCTCTT CCTTCTTTCC TTTTTTTTC AATCCCCATT   119

CATATTCTTT TTTTAGAATA ATCT ATG GCG GCA TCT GTC GAA AAC AGG CAG    170
                          Met Ala Ala Ser Val Glu Asn Arg Gln       9

TTC AGT CAC CTA GAA Gcc GGT TTA TCC CGG TCT TTC AAG CCC CGG       215
Phe Ser His Leu Glu Ala Gly Leu Ser Arg Ser Phe Lys Pro Arg        24

TCT GAT TCC CCG GTT CGT GGC TGC AAC TTC CCT TCG CCC AAC AGT       260
Ser Asp Ser Pro Val Arg Gly Cys Asn Phe Pro Ser Pro Asn Ser        39

ACT AAT TTC CAA AAG AAA CCA AAT TCC ACC ATT TAC CTT GAT TAC       305
Thr Asn Phe Gln Lys Lys Pro Asn Ser Thr Ile Tyr Leu Asp Tyr        54

TCG TCG AGT GAA GAC GAC GAT GAT GAT GAC GAA AAA AAT GAG TAC       350
Ser Ser Ser Glu Asp Asp Asp Asp Asp Glu Lys Ash Glu Tyr            69

CTT CAA ATG ATT AAA AAA GGG AAT TCA GAG TTA GAG CCA TCT GTT       395
Leu Gln Met Ile Lys Lys Gly Asn Ser Glu Leu Glu Pro Ser Val        84

CAT GAC ACT AGG GAC GAA GGT ACC GCT GAT AAT TGG ATT GAA CGC       440
His Asp Thr Arg Asp Glu Gly Thr Ala Asp Asn Trp Ile Glu Arg        99

AAC TTT TCC ATG ATT CGT CTC ACC GGA AAG CAT CCA TTT AAC TCC       485
Ash Phe Ser Met Ile Arg Leu Thr Gly Lys His Pro Phe Asn Ser       114

GAA CCA CCG TTG AAC CGG CTC ATG CAC CAC GGC TTT ATC ACA CCG       530
Glu Pro Pro Leu Asn Arg Leu Met His His Gly Phe Ile Thr Pro      129

GTC CCA CTT CAT TAC GTT CGT AAC CAT GGA CCG GTT CCC AAG GGC       575
Val Pro Leu His Tyr Val Arg Ash His Gly Pro Val Pro Lys Gly      144

ACG TGG GAT GAC TGG ACC GTG GAA GTC ACG GGA CTA GTG AAG CGT       620
Thr Trp Asp Asp Trp Thr Val Glu Val Thr Gly Leu Val Lys Arg      159

CCT ATG AAA TTC ACA ATG GAC CAG TTG GTT AAC GAA TTC CCT TGT       665
Pro Met Lys Phe Thr Met Asp Gln Leu Val Asn Glu Phe Pro Cys      174

AGA GAA TTG CCC GTT ACG CTT GTT TGT GCT GGC AAT CGA AGG AAA       710
Arg Glu Leu Pro Val Thr Leu Val Cys Ala Gly Ash Arg Arg Lys      189

GAA CAG AAC ATG GTT AAA CAA ACC ATT GGT TTC AAC TGG GGC GCC       755
Glu Gln Ash Met Val Lys Gln Thr Ile Gly Phe Asn Trp Gly Ala      204

GCT GCC GTT TCA ACA ACG ATA TGG CGC GGG GTA CCC CTC CGC GCT       800
Ala Ala Val Ser Thr Thr Ile Trp Arg Gly Val Pro Leu Arg Ala      219

TTG CTA AAA CGG TGC GGT GTT TTT AGC AAG AAT AAA GGG GCG CTT       845
Leu Leu Lys Arg Cys Gly Val Phe Ser Lys Ash Lys Gly Ala Leu      234

AAT GTT TGC TTC GAA GGA GCT GAT GTG TTG CCC GGA GGT GGT GGT       990
Asn Val Cys Phe Glu Gly Ala Asp Val Leu Pro Gly Gly Gly Gly      249

TCA AAG TAT GGA ACC AGC ATT AAG AAG GAA TTT GCA ATG GAT CCA       935
Ser Lys Tyr Gly Thr Ser Ile Lys Lys Glu Phe Ala Met Asp Pro      264
```

*Fig. 3a*

| | |
|---|---|
| GCA CGA GAT ATC ATC GTA GCC TAC ATG CAG AAC GGA GAA AAA TTG<br>Ala Arg Asp Ile Ile Val Ala Tyr Met Gln Asn Gly Glu Lys Leu | 980<br>279 |
| GCA CCC GAC CAC GGG TTT CCA GTA CGA ATG ATA ATT CCA GGA TTC<br>Ala Pro Asp His Gly Phe Pro Val Arg Met Ile Ile Pro Gly Phe | 1025<br>294 |
| ATT GGA GGA AGA ATG GTG AAA TGG ATA AAG AGG ATT ATA GTC ACC<br>Ile Gly Gly Arg Met Val Lys Trp Ile Lys Arg Ile Ile Val Thr | 1070<br>309 |
| ACC CAA GAA TCA GAC AGC TAT TAT CAT TTC AAG GAC AAT AGA GTT<br>Thr Gln Glu Ser Asp Set Tyr Tyr His Phe Lys Asp Asn Arg Val | 1115<br>324 |
| CTT CCT CCC CAT GTT GAT GCT GAA CTT GCA AAT ACC GAA GCA TGG<br>Leu Pro Pro His Val Asp Ala Glu Leu Ala Asn Thr Glu Ala Trp | 1160<br>339 |
| TGG TAC AAG CCA GAG TAT ATC ATC AAT GAG CTT AAT ATT AAC TCT<br>Trp Tyr Lys Pro Glu Tyr Ile Ile Asn Glu Leu Asn Ile Asn Ser | 1205<br>354 |
| GTC ATT ACG ACG CCG TGT CAT GAA GAA ATT TTG CCA ATT AAC GCC<br>Val Ile Thr Thr Pro Cys His Glu Glu Ile Leu Pro Ile Asn Ala | 1250<br>369 |
| TGG ACG ACT CAG CGA CCT TAC ACG TTG AGG GGC TAT TCT TAT TCT<br>Trp Thr Thr Gln Arg Pro Tyr Thr Leu Arg Gly Tyr Ser Tyr Ser | 1295<br>384 |
| GGC GGA GGG AAA AAA GTA ACG CGA GTA GAA GTG ACG TTG GAT GGA<br>Gly Gly Gly Lys Lys Val Thr Arg Val Glu Val Thr Leu Asp Gly | 1340<br>399 |
| GGA GAA ACA TGG CAA GTT AGC ACA CTA GAT CAC CCA GAG AAG CCC<br>Gly Glu Thr Trp Gln Val Ser Thr Leu Asp His Pro Glu Lys Pro | 1385<br>414 |
| ACC AAA TAT GGC AAG TAC TGG TGT TGG TGC TTT TGG TCA CTC GAG<br>Thr Lys Tyr Gly Lys Tyr Trp Cys Trp Cys Phe Trp Ser Leu Glu | 1430<br>429 |
| GTT GAG GTG TTA GAC TTG CTC AGT GCT AAA GAA ATT GCT GTT CGA<br>Val Glu Val Leu Asp Leu Leu Ser Ala Lys Glu Ile Ala Val Arg | 1475<br>444 |
| GCT TGG GAT GAG ACC CTC AAT ACT CAA CCC GAG AAG CTT ATT TGG<br>Ala Trp Asp Glu Thr Leu Asn Thr Gln Pro Glu Lys Leu Ile Trp | 1520<br>459 |
| AAC GTC ATG GGA ATG ATG AAT AAT TGC TGG TTC CGA GTA AAG ATG<br>Asn Val Met Gly Met Met Asn Asn Cys Trp Phe Arg Val Lys Met | 1565<br>474 |
| AAT GTG TGC AAG CCT CAC AAG GGA GAG ATT GGA ATA GTG TTT GAG<br>Asn Val Cys Lys Pro His Lys Gly Glu Ile Gly Ile Val Phe Glu | 1610<br>489 |
| CAT CCG ACT CAA CCT GGA AAC CAA TCA GGT GGA TGG ATG GCG AAG<br>His Pro Thr Gln Pro Gly Asn Gln Ser Gly Gly Trp Met Ala Lys | 1655<br>504 |
| GAG AGA CAT TTG GAG ATA TCA GCA GAG GCA CCT CAA ACA CTA AAG<br>Glu Arg His Leu Glu Ile Ser Ala Glu Ala Pro Gln Thr Leu Lys | 1700<br>519 |
| AAG AGT ATC TCA ACT CCA TTC ATG AAC ACA GCT TCC AAG ATG TAC<br>Lys Ser Ile Ser Thr Pro Phe Met Asn Thr Ala Ser Lys Met Tyr | 1745<br>534 |
| TCC ATG TCC GAG GTC AGG AAA CAC AGC TCT GCT GAC TCT GCT TGG<br>Ser Met Ser Glu Val Arg Lys His Ser Ser Ala Asp Ser Ala Trp | 1790<br>549 |
| ATC ATA GTC CAT GGT CAT ATC TAT GAC GCC ACG CGT TTC TTG AAA<br>Ile Ile Val His Gly His Ile Tyr Asp Ala Thr Arg Phe Leu Lys | 1835<br>564 |
| GAT CAC CCT GGT GGG ACT GAC AGC ATT CTC ATC AAT GCT GGC ACT<br>Asp His Pro Gly Gly Thr Asp Ser Ile Leu Ile Asn Ala Gly Thr | 1880<br>579 |

Fig. 3b

```
GAT TGC ACT GAG GAA TTT GAT GCA ATT CAT TCT GAT AAG GCT AAG      1925
Asp Cys Thr Glu Glu Phe Asp Ala Ile His Ser Asp Cys Ala Lys       594

AAG CTC TTG GAG GAT TTC AGG ATT GGT GAA CTC ATA ACT ACT GGT      1970
Lys Leu Leu Glu Asp Phe Arg Ile Gly Glu Leu Ile Thr Thr Gly       609

TAC ACC TCT GAC TCT CCT GGC AAC TCC GTG CAC GGA TCT TCT TCC      2015
Tyr Thr Ser Asp Ser Pro Gly Asn Ser Val His Gly Ser Ser Ser       624

TTC AGC AGC TTT CTA GCA CCT ATT AAG GAA CTT GTT CCA GCG CAG      2060
Phe Ser Ser Phe Leu Ala Pro Ile Lys Glu Leu Val Pro Ala Gln       639

AGG AGT GTG GCC CTA ATT CCA AGA GAG AAA ATC CCA TGC AAA CTC      2105
Arg Ser Val Ala Leu Ile Pro Arg Glu Lys Ile Pro Cys Lys Leu       654

ATC GAC AAG CAA TCC ATC TCC CAT GAT GTT AGG AAA TTT CGA TTT      2150
Ile Asp Lys Gln Ser Ile Ser His Asp Val Arg Lys Phe Arg Phe       669

GCA TTG CCC TCT GAG GAT CAA GTC TTG GGC TTG CCT GTT GGA AAA      2195
Ala Leu Pro Ser Glu Asp Gln Val Leu Gly Leu Pro Val Gly Lys       684

CAT ATC TTC CTC TGT GCC GTT ATT GAC GAT AAG CTC TGC ATG CGC      2240
His Ile Phe Leu Cys Ala Val Ile Asp Asp Lys Leu Cys Met Arg       699

GCT TAC ACG CCT ACT AGC ACG ATC GAT GAG GTG GGG TAC TTC GAG      2285
Ala Tyr Thr Pro Thr Ser Thr Ile Asp Glu Val Gly Tyr Phe Glu       714

TTG GTT GTC AAG ATA TAC TTC AAA GGA ATT CAC CCT AAA TTC CCC      2330
Leu Val Val Lys Ile Tyr Phe Lys Gly Ile His Pro Lys Phe Pro       729

AAT GGA GGG CAA ATG TCA CAG TAT CTT GAT TCT ATG CCG TTA GGG      2375
Asn Gly Gly Gln Met Ser Gln Tyr Leu Asp Ser Met Pro Leu Gly       744

TCA TTT CTC GAC GTG AAA GGT CCA TTA GGT CAC ATT GAA TAC CAA      2420
Ser Phe Leu Asp Val Lys Gly Pro Leu Gly His Ile Glu Tyr Gln       759

GGA AAG GGA AAT TTC TTA GTT CAT GGC AAA CAG AAG TTT GCC AAG      2465
Gly Lys Gly Asn Phe Leu Val His Gly Lys Gln Lys Phe Ala Lys       774

AAG TTG GCC ATG ATA GCA GGT GGA ACA GGA ATA ACT CCA GRG TAT      2510
Lys Leu Ala Met Ile Ala Gly Gly Thr Gly Ile Thr Pro Val Tyr       789

CAA GTC ATG CAG GCA ATT CTG AAA GAT CCA GAA GAT GAC ACA GAA      2555
Gln Val Met Gln Ala Ile Leu Lys Asp Pro Glu Asp Asp Thr Glu       804

ATG TAT GTG GTG TAT GCT AAC AGA ACA GAG GAT GAT ATT TTA CTT      2600
Met Tyr Val Val Tyr Ala Asn Arg Thr Glu Asp Asp Ile Leu Leu       819

AAG GAA GAG CTT GAT TCA TGG GCT GAG AAA ATT CCA GAG AGG GTT      2645
Lys Glu Glu Leu Asp Ser Trp Ala Glu Lys Ile Pro Glu Arg Val       834

AAA GTT TGG TAT GTG GTT CAG GAT TCT ATT AAA GAA GGA TGG AAG      2690
Lys Val Trp Tyr Val Val Gln Asp Ser Ile Lys Glu Gly Trp Lys       849

TAC AGC ATT GGT TTT ATT ACA GAA GCC ATT TTG AGA GAA CAT ATC      2735
Tyr Ser Ile Gly Phe Ile Thr Glu Ala Ile Leu Arg Glu His Ile       864

CCT GAG CCA TCT CAC ACA ACA CTG GCT TTG GCT TGT GGA CCA CCT      2780
Pro Glu Pro Ser His Thr Thr Leu Ala Leu Ala Cys Gly Pro Pro       879

CCT ATG ATT CAA TTT GCT GTT AAT CCA AAC TTG GAG AAG ATG GGC      2825
Pro Met Ile Gln Phe Ala Val Asn Pro Asn Leu Glu Lys Met Gly       894
```

*Fig. 3C*

```
TAT GAC ATT AAG GAT TCC TTA TTG GTG TTC TAATTTTAAAAACAAAACAA         2875
Tyr Asp Ile Lys Asp Ser Leu Leu Val Phe                               904

TATCTGCAGGAATAAATTTTTTTTTCCCCCTATCAGTTGTACATATTGTATTTGGTTTA          2935

TCACCCCCATGTACTACGTAGTGTTTGTAGTTCTTACATTTTTATTTTTAGAATTTTTT          2995

TAAACCTTAGGATATAAAGGTTTTCTCTTCCAACAAAGTGATTCTTTAGGGAAGAAATGT         3055

ACTGTACTGTACTAGTATGTCTAAGCCGAAAGTTGTAATGTTACCATGACAAATTGTAT          3115

TCAATTCCTCATGGAATAGTAACATTGTGTTCATGTGTCTTCCTGTAAGCGATCTTCAAA        3175

ATATCAATGTATATATATAGTAATTGCAAACCATTGTTCCTTTTCCCGATGTAGTTAACT        3235

ACTCTTTCTTTAGCTTCTAGTCTCTGGTGAATATTTTTTTTTCTATAACTCTTTAATTAA        3295

TACGGCCTTAAATAAGAGAAAAGTTTAAACCACGAATATCATTATGCAGACGTATAGGTA        3355

ATTAATCTACTTTTTGAAAAAAAATCTATTTTCTTTATGTGGTCCTTCAAAATAATATTC        3415

TAGAACCTTTTGTATATTCCCTTTTAACTTCTATTTAGTTTT                          3457
```

*Fig. 3d*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 3457 base pairs
        ( B ) TYPE: nucleotide with corresponding protein
        ( C ) STRANDEDNESS: single
        ( D ) TOPOLOGY: linear ( i i ) MOLECULE TYPE: cDNA ( v i ) ORIGINAL SOURCE:
        ( 1 . v i . A ) ORGANISM: Nicotiana tabacum
        ( 1 . v i . B ) CELL LINE: N. tabacum cv. Xanthi XHFD 8

( v i i ) IMMEDIATE SOURCE: leaf (ix) FEATURE:
  (A) NAME/KEY: Nitrate reductase
  (B) LOCATION: from 1 to 143 bp: Leader
      non translated 5 sequence (leader)
  (B) LOCATION: from 144 to 2855 bp: coding sequence
      for nitrate reductase apoenzyme
  (B) LOCATION: from 2856 to 3457 bp: non translated
      3 sequence (xi) SEQUENCE DESCRIPTION: SEQ ID NO:1:

```
GAGCTCGTTC CCAAACAGAA CAAGAAAATC AAATCTCGGA GAGAGAGAGA GAGAAATATT        60

TTGAGAGAGA AATACAGAAA ATCTCTCTTC CTTCTTTCCT TTTTTTTTCA ATCCCCATTC       120

ATATTCTTTT TTTAGAATAA TCT ATG                                           146
                         Met
                          1

GCG GCA TCT GTC GAA AAC AGG CAG TTC AGT CAC CTA GAA GCC GGT TTA         194
Ala Ala Ser Val Glu Asn Arg Gln Phe Ser His Leu Glu Ala Gly Leu
         5                  10                 15

TCC CGG TCT TTC AAG CCC CGG TCT GAT TCC CCG GTT CGT GGC TGC AAC         242
Ser Arg Ser Phe Lys Pro Arg Ser Asp Ser Pro Val Arg Gly Cys Asn
         20                 25                 30

TTC CCT TCG CCC AAC AGT ACT AAT TTC CAA AAG AAA CCA AAT TCC ACC         290
Phe Pro Ser Pro Asn Ser Thr Asn Phe Gln Lys Lys Pro Asn Ser Thr
     35                  40                 45

ATT TAC CTT GAT TAC TCG TCG AGT GAA GAC GAC GAT GAT GAT GAC GAA         338
Ile Tyr Leu Asp Tyr Ser Ser Ser Glu Asp Asp Asp Asp Asp Asp Glu
50                  55                  60                 65

AAA AAT GAG TAC CTT CAA ATG ATT AAA AAA GGG AAT TCA GAG TTA GAG         386
Lys Asn Glu Tyr Leu Gln Met Ile Lys Lys Gly Asn Ser Glu Leu Glu
             70                  75                 80

CCA TCT GTT CAT GAC ACT AGG GAC GAA GGT ACC GCT GAT AAT TGG ATT         434
Pro Ser Val His Asp Thr Arg Asp Glu Gly Thr Ala Asp Asn Trp Ile
             85                  90                 95

GAA CGC AAC TTT TCC ATG ATT CGT CTC ACC GGA AAG CAT CCA TTT AAC         482
Glu Arg Asn Phe Ser Met Ile Arg Leu Thr Gly Lys His Pro Phe Asn
         100                 105                 110

TCC GAA CCA CCG TTG AAC CGG CTC ATG CAC CAC GGC TTT ATC ACA CCG         530
Ser Glu Pro Pro Leu Asn Arg Leu Met His His Gly Phe Ile Thr Pro
     115                 120                 125

GTC CCA CTT CAT TAC GTT CGT AAC CAT GGA CCG GTT CCC AAG GGC ACG         578
Val Pro Leu His Tyr Val Arg Asn His Gly Pro Val Pro Lys Gly Thr
130                 135                 140                 145

TGG GAT GAC TGG ACC GTG GAA GTC ACG GGA CTA GTG AAG CGT CCT ATG         626
Trp Asp Asp Trp Thr Val Glu Val Thr Gly Leu Val Lys Arg Pro Met
             150                 155                 160

AAA TTC ACA ATG GAC CAG TTG GTT AAC GAA TTC CCT TGT AGA GAA TTG         674
Lys Phe Thr Met Asp Gln Leu Val Asn Glu Phe Pro Cys Arg Glu Leu
             165                 170                 175

CCC GTT ACG CTT GTT TGT GCT GGC AAT CGA AGG AAA GAA CAG AAC ATG         722
Pro Val Thr Leu Val Cys Ala Gly Asn Arg Arg Lys Glu Gln Asn Met
         180                 185                 190

GTT AAA CAA ACC ATT GGT TTC AAC TGG GGC GCC GCT GCC GTT TCA ACA         770
Val Lys Gln Thr Ile Gly Phe Asn Trp Gly Ala Ala Ala Val Ser Thr
     195                 200                 205

ACG ATA TGG CGC GGG GTA CCC CTC CGC GCT TTG CTA AAA CGG TGC GGT         818
Thr Ile Trp Arg Gly Val Pro Leu Arg Ala Leu Leu Lys Arg Cys Gly
210                 215                 220                 225

GTT TTT AGC AAG AAT AAA GGG GCG CTT AAT GTT TGC TTC GAA GGA GCT         866
Val Phe Ser Lys Asn Lys Gly Ala Leu Asn Val Cys Phe Glu Gly Ala
             230                 235                 240
```

| | | | | | | | | | | | | | | | | |
|---|---|---|---|---|---|---|---|---|---|---|---|---|---|---|---|---|
| GAT | GTG | TTG | CCC | GGA | GGT | GGT | GGT | TCA | AAG | TAT | GGA | ACC | AGC | ATT | AAG | 914 |
| Asp | Val | Leu | Pro | Gly | Gly | Gly | Gly | Ser | Lys | Tyr | Gly | Thr | Ser | Ile | Lys | |
| | | | 245 | | | | | 250 | | | | | 255 | | | |
| AAG | GAA | TTT | GCA | ATG | GAT | CCA | GCA | CGA | GAT | ATC | ATC | GTA | GCC | TAC | ATG | 962 |
| Lys | Glu | Phe | Ala | Met | Asp | Pro | Ala | Arg | Asp | Ile | Ile | Val | Ala | Tyr | Met | |
| | | 260 | | | | | 265 | | | | | 270 | | | | |
| CAG | AAC | GGA | GAA | AAA | TTG | GCA | CCC | GAC | CAC | GGG | TTT | CCA | GTA | CGA | ATG | 1010 |
| Gln | Asn | Gly | Glu | Lys | Leu | Ala | Pro | Asp | His | Gly | Phe | Pro | Val | Arg | Met | |
| | 275 | | | | | 280 | | | | | 285 | | | | | |
| ATA | ATT | CCA | GGA | TTC | ATT | GGA | GGA | AGA | ATG | GTG | AAA | TGG | ATA | AAG | AGG | 1058 |
| Ile | Ile | Pro | Gly | Phe | Ile | Gly | Gly | Arg | Met | Val | Lys | Trp | Ile | Lys | Arg | |
| 290 | | | | | 295 | | | | | 300 | | | | | 305 | |
| ATT | ATA | GTC | ACC | ACC | CAA | GAA | TCA | GAC | AGC | TAT | TAT | CAT | TTC | AAG | GAC | 1106 |
| Ile | Ile | Val | Thr | Thr | Gln | Glu | Ser | Asp | Ser | Tyr | Tyr | His | Phe | Lys | Asp | |
| | | | 310 | | | | | 315 | | | | | 320 | | | |
| AAT | AGA | GTT | CTT | CCT | CCC | CAT | GTT | GAT | GCT | GAA | CTT | GCA | AAT | ACC | GAA | 1154 |
| Asn | Arg | Val | Leu | Pro | Pro | His | Val | Asp | Ala | Glu | Leu | Ala | Asn | Thr | Glu | |
| | | | 325 | | | | | 330 | | | | | 335 | | | |
| GCA | TGG | TGG | TAC | AAG | CCA | GAG | TAT | ATC | ATC | AAT | GAG | CTT | AAT | ATT | AAC | 1202 |
| Ala | Trp | Trp | Tyr | Lys | Pro | Glu | Tyr | Ile | Ile | Asn | Glu | Leu | Asn | Ile | Asn | |
| | | 340 | | | | | 345 | | | | | 350 | | | | |
| TCT | GTC | ATT | ACG | ACG | CCG | TGT | CAT | GAA | GAA | ATT | TTG | CCA | ATT | AAC | GCC | 1250 |
| Ser | Val | Ile | Thr | Thr | Pro | Cys | His | Glu | Glu | Ile | Leu | Pro | Ile | Asn | Ala | |
| | 355 | | | | | 360 | | | | | 365 | | | | | |
| TGG | ACG | ACT | CAG | CGA | CCT | TAC | ACG | TTG | AGG | GGC | TAT | TCT | TAT | TCT | GGC | 1298 |
| Trp | Thr | Thr | Gln | Arg | Pro | Tyr | Thr | Leu | Arg | Gly | Tyr | Ser | Tyr | Ser | Gly | |
| 370 | | | | | 375 | | | | | 380 | | | | | 385 | |
| GGA | GGG | AAA | AAA | GTA | ACG | CGA | GTA | GAA | GTG | ACG | TTG | GAT | GGA | GGA | GAA | 1346 |
| Gly | Gly | Lys | Lys | Val | Thr | Arg | Val | Glu | Val | Thr | Leu | Asp | Gly | Gly | Glu | |
| | | | | 390 | | | | | 395 | | | | | 400 | | |
| ACA | TGG | CAA | GTT | AGC | ACA | CTA | GAT | CAC | CCA | GAG | AAG | CCC | ACC | AAA | TAT | 1394 |
| Thr | Trp | Gln | Val | Ser | Thr | Leu | Asp | His | Pro | Glu | Lys | Pro | Thr | Lys | Tyr | |
| | | | 405 | | | | | 410 | | | | | 415 | | | |
| GGC | AAG | TAC | TGG | TGT | TGG | TGC | TTT | TGG | TCA | CTC | GAG | GTT | GAG | GTG | TTA | 1442 |
| Gly | Lys | Tyr | Trp | Cys | Trp | Cys | Phe | Trp | Ser | Leu | Glu | Val | Glu | Val | Leu | |
| | | 420 | | | | | 425 | | | | | 430 | | | | |
| GAC | TTG | CTC | AGT | GCT | AAA | GAA | ATT | GCT | GTT | CGA | GCT | TGG | GAT | GAG | ACC | 1490 |
| Asp | Leu | Leu | Ser | Ala | Lys | Glu | Ile | Ala | Val | Arg | Ala | Trp | Asp | Glu | Thr | |
| | 435 | | | | | 440 | | | | | 445 | | | | | |
| CTC | AAT | ACT | CAA | CCC | GAG | AAG | CTT | ATT | TGG | AAC | GTC | ATG | GGA | ATG | ATG | 1538 |
| Leu | Asn | Thr | Gln | Pro | Glu | Lys | Leu | Ile | Trp | Asn | Val | Met | Gly | Met | Met | |
| 450 | | | | | 455 | | | | | 460 | | | | | 465 | |
| AAT | AAT | TGC | TGG | TTC | CGA | GTA | AAG | ATG | AAT | GTG | TGC | AAG | CCT | CAC | AAG | 1586 |
| Asn | Asn | Cys | Trp | Phe | Arg | Val | Lys | Met | Asn | Val | Cys | Lys | Pro | His | Lys | |
| | | | 470 | | | | | 475 | | | | | 480 | | | |
| GGA | GAG | ATT | GGA | ATA | GTG | TTT | GAG | CAT | CCG | ACT | CAA | CCT | GGA | AAC | CAA | 1634 |
| Gly | Glu | Ile | Gly | Ile | Val | Phe | Glu | His | Pro | Thr | Gln | Pro | Gly | Asn | Gln | |
| | | | 485 | | | | | 490 | | | | | 495 | | | |
| TCA | GGT | GGA | TGG | ATG | GCG | AAG | GAG | AGA | CAT | TTG | GAG | ATA | TCA | GCA | GAG | 1682 |
| Ser | Gly | Gly | Trp | Met | Ala | Lys | Glu | Arg | His | Leu | Glu | Ile | Ser | Ala | Glu | |
| | | 500 | | | | | 505 | | | | | 510 | | | | |
| GCA | CCT | CAA | ACA | CTA | AAG | AAG | AGT | ATC | TCA | ACT | CCA | TTC | ATG | AAC | ACA | 1730 |
| Ala | Pro | Gln | Thr | Leu | Lys | Lys | Ser | Ile | Ser | Thr | Pro | Phe | Met | Asn | Thr | |
| | 515 | | | | | 520 | | | | | 525 | | | | | |
| GCT | TCC | AAG | ATG | TAC | TCC | ATG | TCC | GAG | GTC | AGG | AAA | CAC | AGC | TCT | GCT | 1778 |
| Ala | Ser | Lys | Met | Tyr | Ser | Met | Ser | Glu | Val | Arg | Lys | His | Ser | Ser | Ala | |
| 530 | | | | | 535 | | | | | 540 | | | | | 545 | |
| GAC | TCT | GCT | TGG | ATC | ATA | GTC | CAT | GGT | CAT | ATC | TAT | GAC | GCC | ACG | CGT | 1826 |
| Asp | Ser | Ala | Trp | Ile | Ile | Val | His | Gly | His | Ile | Tyr | Asp | Ala | Thr | Arg | |
| | | | 550 | | | | | 555 | | | | | 560 | | | |

| | | | | | | | | | | | | | | | | |
|---|---|---|---|---|---|---|---|---|---|---|---|---|---|---|---|---|
| TTC | TTG | AAA | GAT | CAC | CCT | GGT | GGG | ACT | GAC | AGC | ATT | CTC | ATC | AAT | GCT | 1874 |
| Phe | Leu | Lys | Asp | His | Pro | Gly | Gly | Thr | Asp | Ser | Ile | Leu | Ile | Asn | Ala | |
| | | | | 565 | | | 570 | | | | | | 575 | | | |
| GGC | ACT | GAT | TGC | ACT | GAG | GAA | TTT | GAT | GCA | ATT | CAT | TCT | GAT | AAG | GCT | 1922 |
| Gly | Thr | Asp | Cys | Thr | Glu | Glu | Phe | Asp | Ala | Ile | His | Ser | Asp | Lys | Ala | |
| | | 580 | | | | | 585 | | | | | 590 | | | | |
| AAG | AAG | CTC | TTG | GAG | GAT | TTC | AGG | ATT | GGT | GAA | CTC | ATA | ACT | ACT | GGT | 1970 |
| Lys | Lys | Leu | Leu | Glu | Asp | Phe | Arg | Ile | Gly | Glu | Leu | Ile | Thr | Thr | Gly | |
| 595 | | | | | 600 | | | | | 605 | | | | | | |
| TAC | ACC | TCT | GAC | TCT | CCT | GGC | AAC | TCC | GTG | CAC | GGA | TCT | TCT | TCC | TTC | 2018 |
| Tyr | Thr | Ser | Asp | Ser | Pro | Gly | Asn | Ser | Val | His | Gly | Ser | Ser | Ser | Phe | |
| 610 | | | | | 615 | | | | | 620 | | | | | 625 | |
| AGC | AGC | TTT | CTA | GCA | CCT | ATT | AAG | GAA | CTT | GTT | CCA | GCG | CAG | AGG | AGT | 2066 |
| Ser | Ser | Phe | Leu | Ala | Pro | Ile | Lys | Glu | Leu | Val | Pro | Ala | Gln | Arg | Ser | |
| | | | | 630 | | | | | 635 | | | | | 640 | | |
| GTG | GCC | CTA | ATT | CCA | AGA | GAG | AAA | ATC | CCA | TGC | AAA | CTC | ATC | GAC | AAG | 2114 |
| Val | Ala | Leu | Ile | Pro | Arg | Glu | Lys | Ile | Pro | Cys | Lys | Leu | Ile | Asp | Lys | |
| | | | 645 | | | | | 650 | | | | | 655 | | | |
| CAA | TCC | ATC | TCC | CAT | GAT | GTT | AGG | AAA | TTT | CGA | TTT | GCA | TTG | CCC | TCT | 2162 |
| Gln | Ser | Ile | Ser | His | Asp | Val | Arg | Lys | Phe | Arg | Phe | Ala | Leu | Pro | Ser | |
| | | | 660 | | | | | 665 | | | | | 670 | | | |
| GAG | GAT | CAA | GTC | TTG | GGC | TTG | CCT | GTT | GGA | AAA | CAT | ATC | TTC | CTC | TGT | 2210 |
| Glu | Asp | Gln | Val | Leu | Gly | Leu | Pro | Val | Gly | Lys | His | Ile | Phe | Leu | Cys | |
| | | 675 | | | | | 680 | | | | | 685 | | | | |
| GCC | GTT | ATT | GAC | GAT | AAG | CTC | TGC | ATG | CGC | GCT | TAC | ACG | CCT | ACT | AGC | 2258 |
| Ala | Val | Ile | Asp | Asp | Lys | Leu | Cys | Met | Arg | Ala | Tyr | Thr | Pro | Thr | Ser | |
| 690 | | | | | 695 | | | | | 700 | | | | | 705 | |
| ACG | ATC | GAT | GAG | GTG | GGG | TAC | TTC | GAG | TTG | GTT | GTC | AAG | ATA | TAC | TTC | 2306 |
| Thr | Ile | Asp | Glu | Val | Gly | Tyr | Phe | Glu | Leu | Val | Val | Lys | Ile | Tyr | Phe | |
| | | | | 710 | | | | | 715 | | | | | 720 | | |
| AAA | GGA | ATT | CAC | CCT | AAA | TTC | CCC | AAT | GGA | GGG | CAA | ATG | TCA | CAG | TAT | 2354 |
| Lys | Gly | Ile | His | Pro | Lys | Phe | Pro | Asn | Gly | Gly | Gln | Met | Ser | Gln | Tyr | |
| | | | 725 | | | | | 730 | | | | | 735 | | | |
| CTT | GAT | TCT | ATG | CCG | TTA | GGG | TCA | TTT | CTC | GAC | GTG | AAA | GGT | CCA | TTA | 2402 |
| Leu | Asp | Ser | Met | Pro | Leu | Gly | Ser | Phe | Leu | Asp | Val | Lys | Gly | Pro | Leu | |
| | | 740 | | | | | 745 | | | | | 750 | | | | |
| GGT | CAC | ATT | GAA | TAC | CAA | GGA | AAG | GGA | AAT | TTC | TTA | GTT | CAT | GGC | AAA | 2450 |
| Gly | His | Ile | Glu | Tyr | Gln | Gly | Lys | Gly | Asn | Phe | Leu | Val | His | Gly | Lys | |
| | 755 | | | | | 760 | | | | | 765 | | | | | |
| CAG | AAG | TTT | GCC | AAG | AAG | TTG | GCC | ATG | ATA | GCA | GGT | GGA | ACA | GGA | ATA | 2498 |
| Gln | Lys | Phe | Ala | Lys | Lys | Leu | Ala | Met | Ile | Ala | Gly | Gly | Thr | Gly | Ile | |
| 770 | | | | | 775 | | | | | 780 | | | | | 785 | |
| ACT | CCA | GTG | TAT | CAA | GTC | ATG | CAG | GCA | ATT | CTG | AAA | GAT | CCA | GAA | GAT | 2546 |
| Thr | Pro | Val | Tyr | Gln | Val | Met | Gln | Ala | Ile | Leu | Lys | Asp | Pro | Glu | Asp | |
| | | | | 790 | | | | | 795 | | | | | 800 | | |
| GAC | ACA | GAA | ATG | TAT | GTG | GTG | TAT | GCT | AAC | AGA | ACA | GAG | GAT | GAT | ATT | 2594 |
| Asp | Thr | Glu | Met | Tyr | Val | Val | Tyr | Ala | Asn | Arg | Thr | Glu | Asp | Asp | Ile | |
| | | | 805 | | | | | 810 | | | | | 815 | | | |
| TTA | CTT | AAG | GAA | GAG | CTT | GAT | TCA | TGG | GCT | GAG | AAA | ATT | CCA | GAG | AGG | 2642 |
| Leu | Leu | Lys | Glu | Glu | Leu | Asp | Ser | Trp | Ala | Glu | Lys | Ile | Pro | Glu | Arg | |
| | | 820 | | | | | 825 | | | | | 830 | | | | |
| GTT | AAA | GTT | TGG | TAT | GTG | GTT | CAG | GAT | TCT | ATT | AAA | GAA | GGA | TGG | AAG | 2690 |
| Val | Lys | Val | Trp | Tyr | Val | Val | Gln | Asp | Ser | Ile | Lys | Glu | Gly | Trp | Lys | |
| 835 | | | | | 840 | | | | | 845 | | | | | | |
| TAC | AGC | ATT | GGT | TTT | ATT | ACA | GAA | GCC | ATT | TTG | AGA | GAA | CAT | ATC | CCT | 2738 |
| Tyr | Ser | Ile | Gly | Phe | Ile | Thr | Glu | Ala | Ile | Leu | Arg | Glu | His | Ile | Pro | |
| 850 | | | | | 855 | | | | | 860 | | | | | 865 | |
| GAG | CCA | TCT | CAC | ACA | ACA | CTG | GCT | TTG | GCT | TGT | GGA | CCA | CCT | CCT | ATG | 2786 |
| Glu | Pro | Ser | His | Thr | Thr | Leu | Ala | Leu | Ala | Cys | Gly | Pro | Pro | Pro | Met | |
| | | | | 870 | | | | | 875 | | | | | 880 | | |

| ATT | CAA | TTT | GCT | GTT | AAT | CCA | AAC | TTG | GAG | AAG | ATG | GGC | TAT | GAC | ATT | 2834 |
| Ile | Gln | Phe | Ala | Val | Asn | Pro | Asn | Leu | Glu | Lys | Met | Gly | Tyr | Asp | Ile | |
| | | | 885 | | | | | 890 | | | | | 895 | | | |

| AAG | GAT | TCC | TTA | TTG | GTG | TTC | TAATT | TTAAAAACAA | AACAATATCT | | 2880 |
| Lys | Asp | Ser | Leu | Leu | Val | Phe | | | | | |
| | | 900 | | | | | | | | | |

```
GCAGGAATAA  ATTTTTTTT   TCCCCCTATC  AGTTGTACAT  ATTGTATTTG  GTTTATCACC     2940
CCCATGTACT  ACGTAGTGTT  TGTAGTTCTT  ACATTTTTAT  TTTTTAGAAT  TTTTTTAAAC     3000
CTTAGGATAT  AAAGGTTTTC  TCTTCCAACA  AAGTGATTCT  TTAGGGAAGA  AATGTACTGT     3060
ACTGTACTAG  TATGTCTAAG  CCGAAAGTTG  TAATGTTTAC  CATGACAAAT  TGTATTCAAT     3120
TCCTCATGGA  ATAGTAACAT  TGTGTTCATG  TGTCTTCCTG  TAAGCGATCT  TCAAAATATC     3180
AATGTATATA  TATAGTAATT  GCAAACCATT  GTTCCTTTTC  CCGATGTAGT  TAACTACTCT     3240
TTCTTTAGCT  TCTAGTCTCT  GGTGAATATT  TTTTTTTCTA  TAACTCTTTA  ATTAATACGG     3300
CCTTAAATAA  GAGAAAAGTT  TAAACCACGA  ATATCATTAT  GCAGACGTAT  AGGTAATTAA     3360
TCTACTTTTT  GAAAAAAAAT  CTATTTTCTT  TATGTGGTCC  TTCAAAATAA  TATTCTAGAA     3420
CCTTTTGTAT  ATTCCCTTTT  AACTTCTATT  TAGTTTT                                3457
```

METHOD FOR ENHANCING THE EARLINESS OF A PLANT AND/OR LOWERING THE CONTENT OF NITRATES STORED IN THE PLANT

BACKGROUND

1. Field of the Invention

The present invention relates to a method for improving the earliness of plants, in particular higher plants. The present invention also relates to a method for lowering the content of nitrates stored in plants, in particular in the leaves, where appropriate.

Cultivated species have a reproductive cycle whose duration often limits utilization in the northern regions. In effect, it has to be possible for harvesting of the species to be performed before the return of adverse weather conditions. In many instances, ripening of the harvested organs and the seeds cannot be obtained in good time, and makes it necessary to harvest before maturity, or jeopardizes the crop. Thus, many species such as soybean are cultivated only below certain latitudes for this reason. Moreover, species already cultivated in northern zones, or at altitude, would gain by having a shorter cycle for the same reasons.

This type of problem is traditionally remedied either by using artificial cultivation conditions (greenhouse cultivation), a method which can be exploited for market garden crops, or by selecting for enhanced earliness. A gain in earliness may be obtained either by shortening the duration of the vegetative growth phase, or by accelerating floral induction, or lastly by facilitating the ripening of the fruits or seeds to be harvested. In general, the duration of the vegetative growth phase appears to be controlled by a complex set of genes, and behaves as a quantitative character. There is no indication of causal link between this duration and a particular aspect of the plant's metabolism.

The objective of the present invention is to provide a method that enables the duration of the vegetative phase to be shortened, and hence a gain in earliness to be obtained.

Hence, in the present application as well as in the technical field of the present invention, "early" is understood to denote varieties for which the time elapsing between planting of the seed and the subsequent harvesting is reduced. An "enhanced earliness" implies a shorter duration of the growth phase of the plant, which leads to a flowering and a ripening of the fruits or seeds to be harvested which occur further ahead in time than is normally the case.

Another objective of the present invention was to lower the nitrate content of certain plants, in particular in the leaves. The high nitrate level can, in effect, induce risks to health, as well as displeasure from the standpoint of the organoleptic properties of certain plants, especially for spinach, lettuce or carrot. For this reason, the nitrate contents in edible plants are now subject to control in many countries.

2. Description of the State of the Art

Nitrate reductase is a key enzyme which is known to come into play in the first step of nitrate assimilation in plants.

Nitrate is the most important source of nitrogen for higher plants. Nitrate is absorbed by the roots, transported to various tissues of the plant and then reduced to aqueous ammonia in two steps. The first step requires the enzyme nitrate reductase (NR), which catalyzes the reduction of nitrate to nitrite in the cytoplasm. In a second step, the nitrite is then reduced in the chloroplast by nitrite reductase. The reduction of nitrate is considered to be a major controlling step in nitrate assimilation, and it has been studied in detail in higher plants (Wray, 1986). NR is a homodimer bearing three cofactors, namely FAD, cytochrome $b_{557}$ and a molybdopterin cofactor (Campbell, 1988).

Introduction of the NR gene into a plant has been proposed for modifying the characteristics of nitrate assimilation by plants on an exploratory or speculative basis, but it has not actually been possible to find any real application hitherto.

In any case, the use was always limited to the modulation of nitrate assimilation over time, that is to say according to the stage of development of the plant, or in space, that is to say in order to further assimilation in the roots, tubers or leaves.

SUMMARY OF THE INVENTION

It was discovered unexpectedly that the overexpression of nitrate reductase in transgenic plants into which an NR gene was introduced, on the one hand enabled the nitrate contents stored in reserve form in the plant to be lowered significantly, and on the other hand manifested itself in greater earliness, with a gain in earliness of germination, increased growth and earlier flowering, that is to say a faster vegetative development of the plant which causes it to come to flower approximately two weeks ahead of control plants.

An effect of nitrate reductase overexpression on earliness is unexpected. There is no work covering such studies in the literature. In cereals, a possible effect of the amount of nitrate reductase on yields has been studied by many authors (Clark, 1990). However, when these studies were carried out, no obvious relationship between expression of the enzyme and earliness was noted.

Neither has recent work in genetics enabled direct relationships to be established between the amount of nitrate reductase expressed in the leaves and the transport or storage of nitrate in various species. The study of mutants, deficient for the enzyme nitrate reductase, of *Nicotiana plumbaginifolia* (Saux et al., 1987) or of barley (Warner and Huffaker, 1989) has established that these mutants accumulate nitrate in the leaves at a level comparable with control plants capable of assimilating nitrate. Hence nitrate reductase is not required for nitrate transport. Moreover, various pieces of work studying the genetic control of nitrate content, carried out by Ostrem and Collins (1983) in tobacco and by Blim-Zandstra and Eenink (1986) in lettuce, led to the conclusion that there was no clear correlation, either, between foliar nitrate content and the amount of foliar nitrate reductase. This absence of correlation has been explained by the fact that, since nitrate reductase is itself inducible with nitrate (Crawford, 1989), the accumulation or reduction in content of nitrate may be accompanied by an increase or a reduction, respectively, in the amount of this enzyme in the tissues, by a feedback effect. On the other hand, various authors have put forward the hypothesis that the plant's requirement for osmotically active material might be the factor governing its nitrate storage characteristics, and not the utilization of nitrate by nitrate reductase. The reduction of nitrate content and the enhanced earliness of plants which overexpress nitrate reductase are hence seen to be unexpected.

In either case, the mechanism and the theoretical justifications for explaining these properties are lacking.

The subject of the present invention is hence a method for enhancing the earliness of a plant and/or lowering the content of nitrates stored in the plant, characterized in that an overexpression of the enzyme nitrate reductase is induced in the plant. In other words, an overexpression of nitrate reductase activity is induced in the plant.

"Nitrate reductase" (NR) is understood here to imply a functional definition which includes any nitrate reductase capable of functioning as a selectable marker by conferring nitrate reductase activity on a host cell deficient in nitrate reductase. This definition also includes any nitrate reductase capable of functioning in a given plant so as to enhance the nitrate reductase activity of the said plant. This term hence includes not only the enzyme specific to the specific plant to be treated, but any other nitrate reductase enzyme of other plants, microbes or even other eukaryotic species, if this nitrate reductase is capable of functioning in the plants to be treated.

"Overexpression" is understood to mean both an increase in the level of NR activity relative to the level expressed in a normal plant, and a deregulation of expression leading to the expression of NR activity in a tissue or at a stage of development where this activity is not normally expressed.

The obtaining of plants which express nitrate reductase in a deregulated manner may be obtained by different approaches:

1) By selecting mutants of the plant to be improved, which mutants overexpress nitrate reductase;
2) By introducing by genetic engineering methods a nitrate reductase gene optionally modified in a suitable manner for obtaining the modification of the expression, and preferably the overexpression, of nitrate reductase in the plant to be improved;
3) By introducing simultaneously by genetic engineering methods a nitrate reductase gene and a nitrite reductase gene, optionally modified in a suitable manner for obtaining the modification of the expression, and preferably the simultaneous deregulated overexpression, of these two enzymes in the plant to be improved.
4) By introducing by genetic engineering methods a gene for regulating the expression of nitrate reductase and of nitrite reductase, optionally modified in a suitable manner for obtaining the modification of the expression, and preferably the joint deregulated overexpression, of nitrate reductase and of nitrite reductase in the plant to be improved.

These plants may be modified by the genetic engineering methods described in the literature, by transformation of cells followed by their regeneration, or by transformation of tissues or of gametes.

In a preferred embodiment of the method of the invention, characterized in that a foreign gene coding for nitrate reductase is introduced into the genome of the plant under conditions permitting its expression.

"Functional gene coding for NR" is understood to mean a DNA sequence coding for a polypeptide such as is defined above as "nitrate reductase"; said sequence can hence be shorter or longer than the total coding sequence of the complete gene for the enzyme. In particular, the "functional gene" may correspond to a partial coding sequence, namely one lacking introns.

The foreign gene is, in general, a heterologous gene, that is to say one which originates from an organism of a species different from the host cell, the gene coding for a polypeptide not ordinarily produced by the plant into the genome of which it is introduced.

The foreign gene introduced into the genome of the plant can also be a gene homologous to the endogenous gene, that is to say one whose expression produces the nitrate reductase ordinarily produced by the plant.

"Conditions permitting its expression" is understood to mean that the gene encoding nitrate reductase is placed under the control of elements providing for its expression.

In particular, the DNA sequence coding for nitrate reductase is combined with a regulatory sequence suitable for its transcription and its translation (hereinafter designated regulon), such as promoters, including start and stop codons, enhancers and operators. The means and methods for identifying and selecting these promoters are well known to a person skilled in the art.

According to another embodiment, it is possible merely to act on the regulation of the endogenous nitrate reductase gene by modifying the regulatory genes which contribute to its expression, so that they induce an overexpression of endogenous nitrate reductase as a result of these modifications; in particular, the nitrate reductase gene is placed under the control of a strong heterologous promoter which is functional in the transformed plant.

Moreover, it was discovered according to the present invention that the endogenous promoter of plant nitrate reductase genes requires the presence of sugar in order to be activated and to induce the expression of nitrate reductase; the sugar content in the plant accordingly constitutes a limiting factor, especially at low light intensities.

For this reason, advantageously, when the endogenous or foreign nitrate reductase gene is placed under the control of a heterologous promoter, the heterologous promoter used will preferably not be dependent on the sugar content.

Thus, the 35S promoter of CaMV (Kray, Chan, Daly and McPherson, 1987), or the promoter of the gene coding for the translation elongation factor (Curie et al., 1991), or any other promoter whose functioning does not depend on the presence of sugar, are advantageously used for this purpose. Likewise, suitably, promoters which are inducible by a lack of carbon assimilates derived from photosynthesis may be employed.

For this reason also, according to another embodiment of the method of the invention, the sugar content in the plant is merely increased in order to further endogenous nitrate reductase expression without introducing a foreign gene.

As a heterologous gene coding for a nitrate reductase, special mention may be made of plant genes, in particular those of dicotyledons such as tobacco (Vaucheret et al., 1989), tomato (Daniel-Vedele et al. 1989), Arabidopsis (Crawford et al., 1988) and bean (Hoff, Stummann and Henningssen, 1991), or of monocotyledons such as barley (Kleinhofs et al., 1988) and rice (Chol, Kleinhofs and An, 1989).

It should hence be clearly understood that the invention involves not only the use of cDNAs encoding the nitrate reductase originating, in particular, from plants, but also any equivalent DNA sequence, that is to say which differs from the cDNA sequence only in one or more neutral mutations, that is to say ones in which the change or substitution of nucleotides in question does not affect the primary sequence of the resulting protein.

The present invention also involves the use of DNA sequences complementary to the sequences mentioned above, especially ones which display sufficient homology with a cDNA sequence complementary to the mRNA of a nitrate reductase, such that they hybridize with said cDNA sequence to the extent of 80% under stringent conditions.

In fact, the nitrate reductases of different dicotyledonous species display great homology. Thus, tomato nitrate reductase displays approximately 90% homology with tobacco nitrate reductase, and the DNA sequence encoding tomato nitrate reductase displays more then 80% homology (approximately 81%) with the DNA sequence encoding tobacco nitrate reductase.

The nitrate reductases are characterized especially by the presence of the following invariant amino acids (Daniel-Vedele, Dorbe, Caboche and Rouzé, 1989) in the coding sequence of the enzyme (positions supplied relative to the amino acid sequence of tobacco nitrate reductase):

Sequence CAGNRRKE of amino acids 180 to 187 of the molybdenum-containing cofactor binding domain of the enzyme, Sequence HPGG of amino acids 564 to 567 of the cytochrome $b_5$ domain of the enzyme, Sequence GLP of amino acids 677 to 679 of the cytochrome $b_5$ reductase domain of the enzyme.

Patent Applications EP 283,338 and EP 409,730 describe DNA sequences coding for tobacco and tomato nitrate reductases, respectively.

Said functional gene coding for nitrate reductase may be introduced into plant cells according to known techniques. The constitutive regulon of the nitrate reductase gene may advantageously be used in this case, but it is not essential to do so.

There may be mentioned, in the first place, methods of direct gene transfer such as direct micro-injection into embryo cells of the plant (Neuhaus et al., 1987) or electroporation (Chupeau et al., 1988), or alternatively direct precipitation by means of PEG (Schocher et al., 1986) or bombardment with a particle gun (Mc Cabe et al., 1988).

It is also possible to infect the plant with a bacterial strain, in particular of *Agrobacterium tumefaciens* according to a proven method (Schell and Van Montagu, 1983) or of *Agrobacterium rhizogenes*, in particular for species refractory to transformation (Chilton et al., 1982). The bacterial strain will contain the gene Coding for nitrate reductase under the control of elements providing for the expression of said gene. The strain may be transformed with a vector into which is inserted the gene coding for nitrate reductase under the control of elements providing for the expression of said gene. This gene will be inserted, for example, into a binary vector such as pBIN19 (Bevan, 1984) or pMON 505 (Horsch and Klee, 1986) or any other binary vector derived from Ti and Ri plasmids. It may also be usefully introduced by homologous recombination into a disarmed Ti or Ri plasmid, such as pGV 3850 (Zambryski et al., 1983) before transformation of the plant.

As an expression vector comprising the functional nitrate reductase gene according to the invention, vectors comprising a DNA sequence containing at least one origin of replication, such as plasmids, cosmids, bacteriophages, viruses, and the like, may be mentioned. Plasmids will nevertheless be preferably used.

When a functional gene coding for a nitrate reductase is introduced into the genome of the plant, it will preferably be under the control of a heterologous promoter.

By way of illustration, there may be mentioned in this connection constitutive promoters such as that of the translation elongation factor (Curie et al., 1991), tissue-specific promoters such as that of patatin, which is expressed in tubers (Rocha-Sosa et al., 1989) or such as that of the small subunit of ribulosebisphosphate decarbosylase which are expressed in the leaves (Thomson and White, 1991), or those derived from plant viruses, such as the 35S promoter of cauliflower mosaic virus or CaMV (Kay, Chan, Daly and McPherson, 1987) or derived from the T-DNA of Agrobacteria or any source of functional promoter in the transformed plant.

In the examples below, given purely by way of illustration, the foreign gene coding for nitrate reductase is derived from the Nia 2 gene for nitrate reductase of tobacco, described in FIG. 3 (Vaucheret et al., 1989), and the foreign gene coding for nitrate reductase is inserted into plasmid pBin 19.

Lastly, the subject of the present invention is transgenic plants displaying enhanced earliness and/or having reduced contents of stored nitrates, obtained by the method according to the invention.

As transgenic plants according to the invention, all edible plants cultivated in the greenhouse or in the field may be mentioned, and in particular tobacco, lettuce, spinach, carrot and the different varieties of cabbage.

The characteristics of plants expressing nitrate reductase in a deregulated manner, jointly or otherwise with the deregulated expression of nitrite reductase, are a gain in earliness of germination, an enhanced growth and an earlier flowering.

Furthermore, this deregulated expression manifests itself in additional characteristics such as:

a fall in the nitrate content in the tissues of the plant, and that of conferring on the plants obtained a characteristic which enables them to be distinguished readily from unmodified plants as a result of the enhanced sensitivity of the modified plants to chlorate.

Chlorate is used as a defoliant. Chlorate treatment proves useful prior to the harvesting of some plants at maturity, such as cotton.

Thus, it is possible, as a result of the method of the invention, to use chlorate at smaller doses in order to induce the defoliation of plants which are modified according to the invention if this treatment proves useful.

Other characteristics and advantages of the present invention will become apparent in the light of the detailed description of the embodiment which follows.

DESCRIPTION OF THE DRAWINGS

FIG. 3A, 3B, 3C and 3D show the sequence of the gene derived from Nia2 for nitrate reductase of tobacco stripped of its introns.

DESCRIPTION OF THE PREFERRED EMBODIMENT

Example 1

Effect of the Overexpression of Nitrate Reductase on the Earliness of Tobacco

Recombinant genes derived from the nitrate reductase gene of tobacco (European Patent EP 283,338) were initially produced according to a traditional procedure described by Vincentz and Caboche (1991) in order to complement *N. plumbaginifolia* mutants deficient for nitrate reductase. These genes are made up as follows. The nitrate reductase coding sequence (cDNA derived from messenger of Nia2 origin), preceded or otherwise by the untranslated 5' sequence of this transcript and followed by transcription termination sequences which is derived from one of the nitrate reductase genes of tobacco, or from CaMV, was placed under the control of the 35S RNA strong promoter of CaMV.

In the present example this gene was inserted into a binary vector plasmid pBin19 (BEVAN, 1984) and introduced according to a traditional procedure into the genome of industrial tobaccos, varieties PBD6 and BB16, by means of *Agrobacterium tumefaciens* (strain LBA 4404) (Hoekema et al., 1983). Transformation was carried out by inoculation of foliar disks of average surface area 5 cm$^2$. Plasmid pBin19 carrying the NPTII (neomycin phosphotransferase) gene conferring resistance to kanamycin after transformation, transformants were selected for their ability to grow on a dose of 100 mg/l of this antibiotic. Of a total of 125 explants inoculated for the variety BB16 and 190 explants for the variety PB D6, the number of transformed plants obtained amounts to 10 and 281, respectively. Among these plants, some can reach a level of nitrate reductase activity six times as high as that observed for the wild-type. The germination and growth characteristics of two transformants which overexpress nitrate reductase have been presented here and are representative.

Study of the Growth in Vitro of the Progeny of the Transformant 30.51

Figure 1:
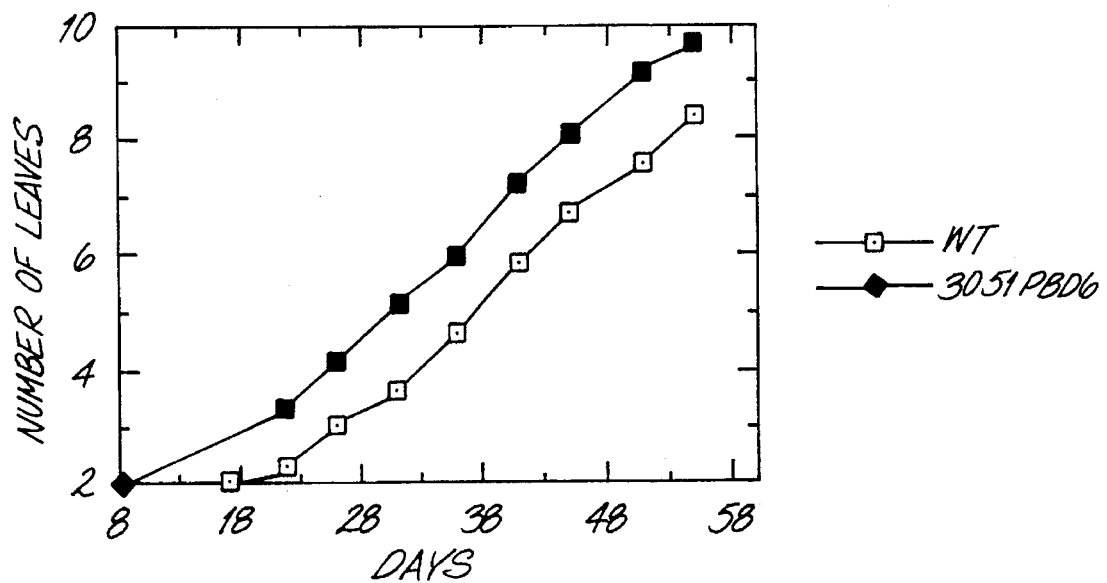
FIG. 1 illustrates a comparative study of the growth of the progeny of transformed tobacco 3051 PBD6, cultivated in vitro. The average number of leaves per plantlet (ordinates) was measured and plotted as a function of the number of days elapsing after sowing (abscissae).

This transformant, obtained from the PBD6 geno-type, overexpresses approximately 600% of the nitrate reductase level of the untransformed control. Its progeny was harvested and studied. After surface sterilization for 40 minutes in a solution of 800 ml of water containing one tablet of Bayrochlore of 1 ml of Teepol, followed by rinsing three times in 800 ml of sterile water, the seeds were sown on propagation medium containing 20 mM nitrate. 12 seeds of this plant, together with an identical number of the wild-type, were cultured in this way in vitro in tubes, and then placed in culture chambers in which the temperature is maintained at 25° C. and the relative humidity at 65%; illumination of these chambers is provided by Philips 40W "industry white" type fluorescent tubes, providing a light intensity of 60 µE m$^{-2}$s$^{-1}$, for 16 hours a day. FIG. 1 shows that the progeny of the transformant germinates significantly earlier than that of the untransformed control. A mean value calculated for each group reveals that the progeny of the transformed plant germinates 9 days before that of the wild-type.

Study of the Growth of the Progeny of the Primary Transformant 30.1 BB16

Figure 2:
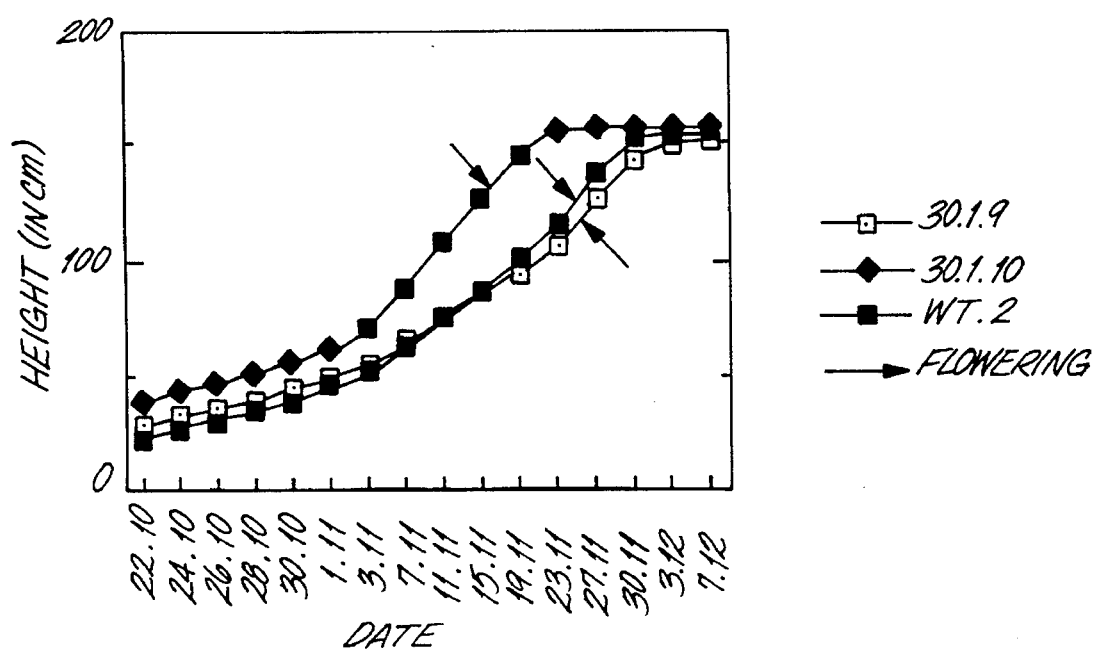
FIG. 2 illustrates the growth in the greenhouse and flowering of plants overexpressing or otherwise nitrate reductase. These plants were planted out in the greenhouse at the same stage of development and cultivated under the same experimental conditions.

The seeds originating from the plant 30.1 BB16 (primary transformant overexpressing the nitrate reductase gene at a level three times as high as the untransformed control) was sown on peat and fed with Coïc and Lesaint nutrient solution containing 20 mM nitrate as nitrogen source. In this way, 10 plants were arranged in the greenhouse under an illumination for 16 hours a day. It emerges from a study thereof (FIG. 2) that plants which constitutively overexpress the nitrate reductase gene (such as the plant 30.1.10, taken as an example) have their flowering advanced by 10 days relative to that of the wild-type (WT.2 and 30.1.9., this latter plant being a wild-type plant which does not overexpress nitrate reductase and is not resistant to kanamycin, which has segregated in the progeny of the primary transformant).

Example 2

Study of the Sensitivity to Chlorate of Transgenic Plants Constitutively Expressing the Nitrate Reductase Gene Pan sowings of homozygous progeny of the transformant 30.51PBD6 were performed in parallel with control sowings. These pans were watered with a solution containing 0.5 mM, 1.5 mM, 5 mM or 10 mM potassium chlorate ten days after sowing, at the two-leaf stage. Whereas control plants manifest the symptoms of chlorosis and then of leaf scorch characteristic of the effect of chlorate only at doses of 5 and 10 mM, the transgenic plants are already killed at the lowest dose of chlorate employed (0.5 mM).

Example 3

Effect of the Overexpression of Nitrate Reductase on Foliar Nitrate Content in *Nicotiana plumbaginifolia*

The nitrate reductase coding sequence (cDNA derived from messenger of Nia2 origin), preceded by the untranslated 5' sequence of this transcript and followed by transcription termination sequences derived from the Nia2 gene for nitrate reductase of tobacco, was placed under the control of the 35S RNA strong promoter of CaMV. In the present example, this gene was inserted into a binary vector plasmid pBin19 and introduced into the genome of the *Nicotiana plumbaginifolia* mutant E23 which is deficient for the nitrate reductase structural gene, according to a traditional procedure described in Example 1. A transformant, C1, expressing a nitrate reductase activity of 29 nM nitrite per minute per mg of total protein, equivalent to 178% of the wild-type control, was studied. Wild-type *Nicotiana plumbaginifolia* plants or those of the C1 transformant were cultivated in the greenhouse at the I.N.R.A. of Versailles during autumn 1990.

a) During the first trial (7/09 to 7/11/90), the plants were placed on a peat/clay mixture and watered twice in 24 h with a nitroco-ammoniacal complete nutrient solution (430 ml per plant per day), containing either 10.2 mM nitrate and 1.8 mM ammonium or 15.3 mM nitrate and 2.7 mM ammonium. The natural illumination was supplemented with extra illumination providing of the order of 100 mmol m$^{-2}$s$^{-1}$ PAR for 16 h (phytoclaude lamps). Harvesting took place at the beginning-of-flowering stage. Analyses were performed on 4 plants, taken at random from among the 28 plants cultivated, per genotype and per type of culture condition.

b) During the second trial (25/10/90 to 30/01/91), the plants were placed on inert sand and watered every 15 minutes for 24 h with a complete nutrient solution (9.6 l per plant per day), containing either 1 mM nitrate alone or 12 mM nitrate alone. The natural illumination was supplemented with extra illumination identical to that of the preceding trial, but for 12 h. The plants were harvested at the rosette stage, and the analyses were performed on an average sample grouping together 4 plants taken at random, from among the 14 plants cultivated, per genotype and per type of culture condition.

The analyses performed after harvesting show the following trends (see attached table):

1) The nitrate content is much lower in the transformed plants than in the control plants (by −30% to −70%);
2) The reduced nitrogen content is higher in the transformed plants. It should be noted that there is a maximum threshold corresponding to 4.5% of reduced nitrogen in all the types of plants, irrespective of the type of nitrogenous nutrition;
3) The protein nitrogen content is the same in the transformed and control plants;
4) The total nitrogen content in the transformed plants is slightly lower than in the control plants;
5) The type of nitrogenous nutrition (in amount and in quality) modifies the content of nitrogen compounds per plant, but does not appear to have an effect on the general behavior of the plants.

In conclusion, the transformed plants accumulate much less nitrogen in nitric form than the control plants. The transformed plants accumulate nitrogen in reduced form. This excess of internal reduced nitrogen might be one of the causes of the greater dry matter (D.M.) content, as well as of the lower production of fresh and dry biomass (by −15% to −30%), observed in the transformed plants.

analyses were performed on the leaves of 4 plants, taken at random, per control or C1 genotype. The level of nitrate reductase transcript was measured by the Northern method (Thomas, 1980) in these leaves. This amount of transcript decreases 20- to 50-fold in the control plants placed in the dark, whereas it decreases by only 50% in the C1 plants placed under the same conditions. The leaves removed from these control plants maintained in the dark and having their petiole dipped for four hours in a preserving solution (40 mM potassium chloride and 10 mM calcium chloride) containing 0.2% of glucose accumulate nitrate reductase transcript again to an approximate level of 25% relative to the initial conditions preceding transfer to the dark. In contrast, this accumulation is not observed in the case of control leaves maintained in the dark and having their petiole dipped in the preserving solution without glucose. In the C1 plants, the level of nitrate reductase transcript remains high in the various steps of the experiment, showing that the reduction in the level of nitrate reductase transcript in the control plants is not the outcome of a general slowing of the metabolism due to the lack of sugar. Hence sugar content is seen to be an important signal for the expression of the unmodified nitrate reductase gene, and can hence constitute a factor limiting this expression at low light intensities.

TABLE 1

FOLIAR TOTAL, NITRIC, REDUCED OR PROTEIN NITROGEN CONTENT OF PLANTS OVEREXPRESSING NITRATE REDUCTASE IN A DEREGULATED MANNER

| | Total N % D.M. | $NO_3^-$ % D.M. | Reduced N* % D.M. | Protein N % D.M. | % D.M. | D.M. g/plant |
|---|---|---|---|---|---|---|
| Trial 1 | | | | | | |
| nutrient solution: $10.2\ mM\ NO_3^- + 1.8\ mM\ NH_4^+$ | | | | | | |
| Control | 4.09 | 1.11 | 2.98 | 2.07 | 10.7 | 19.5 |
| Transformed | 4.03 | 0.67 | 3.36 | 2.12 | 10.4 | 16.4 |
| nutrient solution: $15.3\ mM\ NO_3^- + 2.7\ mM\ NH_4^+$ | | | | | | |
| Control | 4.56 | 1.78 | 2.78 | 2.21 | 8.2 | 18.2 |
| Transformed | 3.80 | 0.53 | 3.27 | 2.17 | 11.6 | 19.7 |
| Trial 2 | | | | | | |
| nutrient solution: $1\ mM\ NO_3^-$ | | | | | | |
| Control | 5.51 | 1.09 | 4.42 | 2.82 | 5.9 | 3.3 |
| Transformed | 5.05 | 0.62 | 4.43 | 2.92 | 6.5 | 2.5 |
| nutrient solution: $12\ mM\ NO_3^-$ | | | | | | |
| Control | 6.06 | 2.14 | 3.92 | 2.89 | 6.0 | 3.95 |
| Transformed | 5.90 | 1.49 | 4.41 | 2.84 | 6.7 | 2.85 |

*calculation of reduced N: total N − $NO_3^-$

Example 4

Role of Sugar in the Expression of Nitrate Reductase

Wild-type and C1 *Nicotiana plumbaginifolia* plants identical to those described in Example 3 were planted out at the 4-leaf stage, and cultivated for three weeks in the greenhouse, at the I.N.R.A. of Versailles during autumn 1990, in a vegetable mold watered with a nitrocoammoniacal complete nutrient solution containing 12 mM nitrate and 2 mM ammonium. The plants were transferred to a culture chamber for 6 days and subjected to a photo-period of 16 hours at 25° C., with an illumination of 130 mE $m^{-2}s^{-1}$ PAR for 16 h (phytoclaude lamps) followed by 8 hours of darkness at 16° C. The plants were then placed in the dark for 72 hours while still being fed with the nutrient solution. At this stage, Example 5

Effect of the Overexpression of Nitrate Reductase on Foliar Nitrate Content in *Nicotiana tabacum*

During a trial, the plants were arranged in three blocks, each comprising 8 plots of 48 plants which received doses of 200 or 400 kg per ha for nitrogen supply. The plants were topped after flowering. The experimental plan per block was determined on a random basis, and 10 plants per plot, taken at random, were subjected to chemical characterization.

Assay Methods

Nitrate Ions

The assay is carried out on a Technicon autoanalyzer AA II C type continuous flow apparatus. 500 mg of lyophilized tobacco are placed in 120 ml of water and stirred for 30 min. The suspension is filtered after the volume has been adjusted to 200 ml. The sample withdrawn is reduced to nitrite ions on a cadmium column and is then mixed with Griess reagent (sulfanilamide 10 g/l; concentrated phosphoric acid 10%; N-naphthylethylenediamine 0.5 g/l). After color-formation, the optical density is read at 560 nm, and the content of nitrate ions is determined by reference to a standard series produced using potassium nitrate.

Nitrite Ions

The contents of nitrite ions are evaluated in a similar manner to that used for the assay of nitrate ions, on a technicon autoanalyzer AA II type apparatus. 500 mg of tobacco powder are placed in 50 ml of extraction solution (KCl 1%; sulfanilamide 0.5%; triton X100 0.2%) and stirred for 30 min. The solution is filtered through Whatman paper, 10 ml of the filtrate are then brought into contact with 500 mg of active charcoal in order to decolorize the tobacco extracts. The sample is then colored with the Griess reagent described above. The absorbance is read at 560 nm, and the content of nitrite ions is determined by reference to a standard series.

Total Nitrogen

Mineralization of the organic matter is carried out in an oven at a temperature of 420° C. 500 mg of tobacco powder are digested with 15 ml of concentrated sulfuric acid in the presence of 1 g of catalyst comprising selenium (0.2 part), copper sulfate (1 part) and potassium sulfate (1 part). After 1 h in the oven, the nitrogen is converted to the form of ammonium sulfate. 50 ml of water are then added, and the aqueous ammonia formed is liberated with an excess of 30% caustic soda and thereafter distilled off by steam distillation in a Técator semi-automatic apparatus. The aqueous ammonia is collected in 20 ml of 2% boric acid and titrated with 0.05N sulfuric acid.

Figure 4:
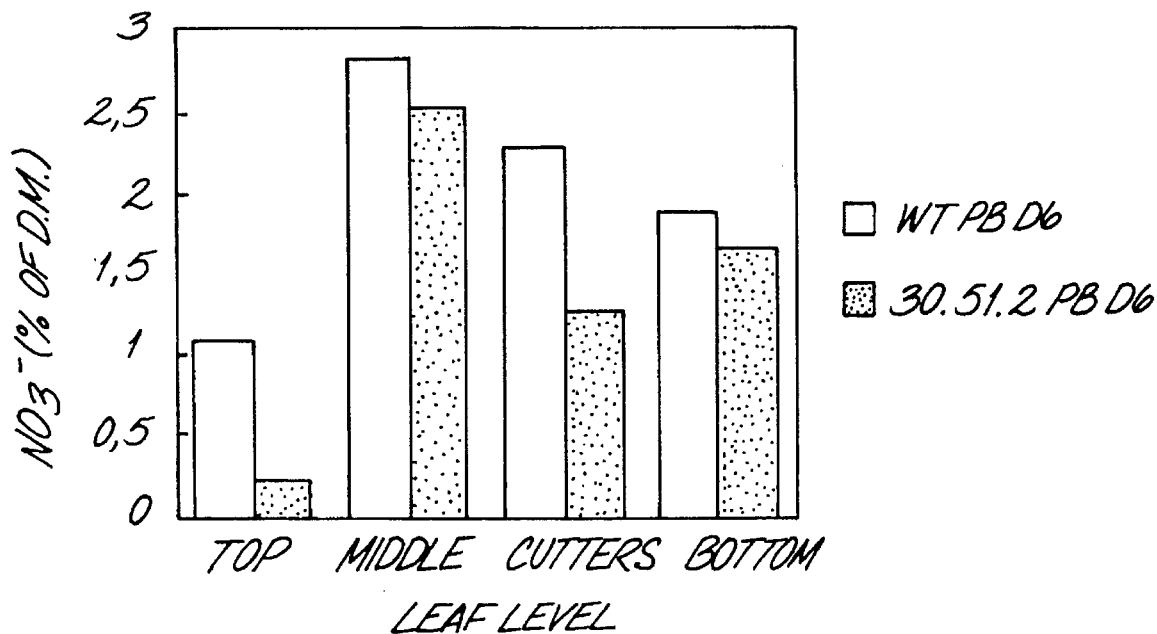
FIG. 4 illustrates the content of nitrate ions of the different leaf levels of the line 30.51.2 PB D6. The plants were cultivated in the field in the presence of 400 kg of nitrogen per ha.
Figure 5:
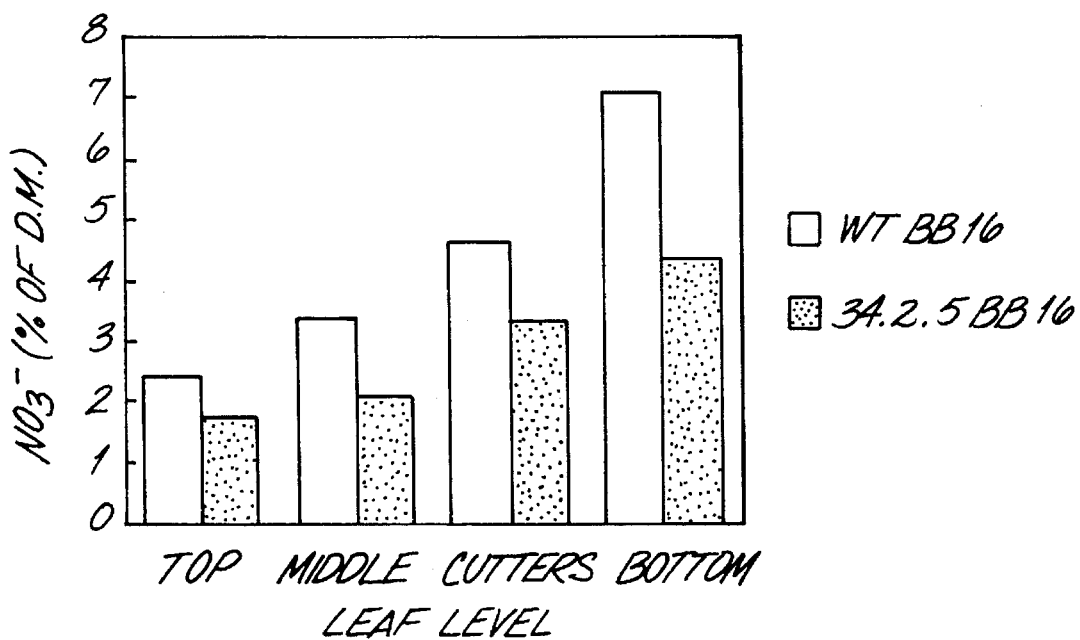
FIG. 5 illustrates the content of nitrate ions of the different leaf levels of the line 34.2.5 BB 16. The plants were cultivated in the field in the presence of 400 kg of nitrogen per ha.

The analyses after harvesting show the following trends (see FIGS. 4 and 5 and Table 2):

1) In the wild-type, the effect of a high dose of nitrogen (400 kg/ha) on growth is very clear, but nitrate ions, in spite of the topping, remain stored in the leaves (Tab. 2). The accumulation of nitrate ions is all the greater in BB 16 for the fact that this variety is a chlorophyll-deficient mutant.

2) The content of nitrate ions of the cutters, which represents the accumulation in tobacco, fall significantly by 38% for such a nitrogen supply, whereas the fall for the line 34.2.5 BB 16 reaches 28%. In the line 30.51.2 PB D6 (FIG. 4), these decreases range, depending on the leaf level, from 11% to 75% for an overall fall of 36%, whereas for the line 34.2.5 BB 16 (FIG. 5), these falls vary from 26% to 39% for an overall value of 33%. The decrease in the amount of nitrate ions accumulated in the leaf is, however, greater in the line 34.2.5 BB 16 than in the line 30.51.2 PB D6, this variety accumulating relatively little nitrate ion.

3) Nitrite ions, while plentiful in the high leaves in the line 34.2.5 PB D6, decrease in the leaves of the base (Tab. 2). Moreover, in the line 30.51.2 PB D6, the depletion of nitrate ions appears to be the source of the fall in nitrite ions. The anticipated accumulation of nitrite ions resulting from the deregulation of the NR gene is hence limited, and tends to fade away at maturity.

4) The nitrogen content of the leaves depends directly on the initial nitrogen supply, but it may be noted that, in the transgenic individuals, the application of the higher dose (400 kg of nitrogen/ha) has no effect on the total nitrogen content (Tab. 2). Only at the lower dose (200 kg of nitrogen/ha) is a difference observed (Tab. 2). The rise in total nitrogen content, which is greatest in the top leaves, is limited to 19% for the line 30.51.2 PB D6 and 31% for the line 34.2.5 BB 16. Although this assessment is limited to the leaves, it nevertheless appears that the absorption of nitrogen is greater.

In conclusion, the transformed plants accumulate less nitrogen in nitric form than the control plants. Nitrogen assimilation in the transformed plants is more efficient, and they accumulate the nitrogen in reduced form.

TABLE 2

Contents of nitrogen compounds of the different leaf levels

| | | N1 = 200 kg of nitrogen/ha | | | N2 = 400 kg of nitrogen/ha | | |
|---|---|---|---|---|---|---|---|
| | | $NO_3^-$ (% of D.M.) | $NO_2^-$ (ppm) | total nitrogen (% of D.M.) | $NO_3^-$ (% of D.M.) | $NO_2^-$ (ppm) | total nitrogen (% of D.M.) |
| WT PB D6 | Top | 0.07 | 70 | 2.18 | 1.12 | 42 | 3.44 |
| | Middle | 0.08 | 121 | 2.08 | 2.84 | 87 | 3.48 |
| | Cutters | 0.21 | 106 | 1.76 | 2.29 | 154 | 2.76 |
| | Bottom | 0.24 | 276 | 1.58 | 1.88 | 214 | 2.76 |
| 30.51.2 | Top | 0* | 48 | 2.60* | 0.25* | 59 | 3.78 |
| | Middle | 0.05* | 96 | 2.34 | 2.54 | 88 | 3.45 |
| | Cutters | 0.10* | 195 | 2.01 | 1.27 | 75* | 3.17 |
| | Bottom | 0.13* | 216 | 1.71* | 1.68 | 279 | 2.68 |
| WT BB 16 | Top | 0.34 | 50 | 3.30 | 2.46 | 47 | 4.73 |
| | Middle | 0.46 | 93 | 2.81 | 3.44 | 127 | 4.52 |
| | Cutters | 1.08 | 108 | 2.73 | 4.69 | 147 | 4.29 |
| | Bottom | 1.49 | 276 | 2.60 | 7.18 | 302 | 4.22 |
| 34.2.5 | Top | 0.65 | 75 | 4.31* | 1.81* | 63 | 4.89 |
| | Middle | 0.84 | 143 | 3.36 | 2.11* | 137 | 4.52 |
| | Cutters | 0.90 | 182 | 3.36* | 3.37* | 183 | 4.40 |
| | Bottom | 1.72 | 207 | 2.90 | 4.39* | 253 | 3.97* |

*Significant effect at the 5% level (Duncan's test)

Example 6

Production of Transformed Lettuces (*Lactuca sativum*)

The nitrate content in lettuce is very high, and exceeds acceptable levels for consumption if the natural illumination of the crop is limited, as is the case in greenhouses during autumn, winter and spring.

An *Agrobacterium tumefaciens* strain (LBA-4404) containing a binary vector plasmid derived from pBin19 (pBCSL16), containing the nitrate reductase gene of tobacco and the nptII (neomycin phosphotransferase) gene, was used for the production of transformed lettuce. The tobacco gene was placed under the control of the same 35S promoter. The constructions used are identical to those of Example 1.

Four varieties of greenhouse lettuce (Flora, Corrina, Luxor and Evola) were used for the transformation experiments. After culturing wounded explants and Agrobacteria (see Michelmore et al., Pl. Cell Rep. 6:439 (1987)), several buds were regenerated by callus formation on a selective culture (100 mg/l of kanamycin). The transformed state of the independent buds was verified by assaying npt II activity. Several of the transformed plants were then transferred to a greenhouse.

Study of the Nitrate Reductase Activity and Foliar Nitrate Content in Transformed Lettuce (Ro generation)

The transformed plants were raised in a greenhouse under favorable conditions. Among the plants, variable phenotypes are observed.

Three weeks after transfer to the greenhouse, the plants were shaded (approximately 1000 lux) for two days. Leaf samples (disks 2 cm in diameter) were then removed for a determination of nitrate reductase activity according to a known method (see Blom. Zandstra. Lamp Plant. Nutr., no. 6–611 (1983)). Table 3 shows that, of the 104 plants transformed, approximately 13% show very high nitrate reductase activity (more than 400%) in comparison with control plants regenerated in vitro. For around twenty primary transformants, the nitrate content was measured according to a traditional procedure described by Sen Donaldson (J. Assoc. Off. Anal. Chem. 61: 1389 (1978)).

In general, the nitrate content was reduced by nearly 50% in plants with a very high nitrate reductase activity. For the most part, the npt II activity was very high in these plants.

TABLE 3

Numbers of plants of primary transgenic lettuce (Ro) and its nitrate reductase (NR) activity measured in vivo

| Genotype | Number of plants with NR activity[1] | | | |
|---|---|---|---|---|
| | 200% | 200–400% | 400% | Total |
| Flora | 11 | 5 | 1 | 17 |
| Luxor | 24 | 9 | 7 | 40 |
| Cortina | 8 | 3 | 2 | 13 |
| Evola | 24 | 7 | 3 | 34 |
| Total | 67 | 24 | 13 | 104 |

[1]Relative activity in comparison with the level of untransformed controls.

TABLE 4

NITRATE REDUCTASE ACTIVITY AND NITRATE CONTENT OF PRIMARY TRANSFORMANT LETTUCES (Ro)

| Genotype | NR activity (relative) | Nitrate content PPM | Nitrate content Reduction (%) |
|---|---|---|---|
| Control Flora | 100 | 3150 | — |
| Transformant Flora 4 | >300 | 1700 | −46 |
| Transformant Flora 32 | ≈200 | 2100 | −33 |
| Control Luxor | 100 | 3730 | — |
| Transformant Luxor 31 | >300 | 2350 | −37 |
| Transformant Luxor 44 | 200–400 | 2100 | −44 |
| Control Cortina | 100 | 4120 | — |
| Transformant Cortina 8 | 200–400 | 2100 | −49 |

FIG. 3 shows a sequence identified as below:
Sequence type: Nucleotide and its corresponding protein
Sequence length: 3457 base pairs
Strandedness: single
Topology: linear
Molecule type: complementary DNA (cDNA)
Original Source
Organism: Plant, *Nicotiana tabacum*
Experimental source: leaves
Line name: *N. tabacum* cv. Xanthi XHFD8
Characteristice
from 1 to 143 base pairs: untranslated 5' sequence (leader)
from 144 to 2855 base pairs: coding sequence for the nitrate reductase apoenzyme
from 2856 to 3457 base pairs: untranslated 3' sequence
Properties
cDNA of the messenger coding for the nitrate reductase apoenzyme

BIBLIOGRAPHY

BEVAN M.—1984—Binary Agrobacterium vectors for plant transformation Nucleic Acid Res. 12: 8711–8712.

BLOM-ZANDSTRA, M. AND EENINK, A. H.—1986—Nitrate concentration and reduction in different genotypes of lettuce J. Amer. Soc. Hort. Sci III: 908–911.

CAMPBELL 1988—Higher plant Nitrate Reductase Curr. Top. Plant Biochem. Physiol. 7.1–15.

CHOI, H., KLEINHOFS A., AND AN, G. (1989) Nucleotide sequence of rice nitrate reductase genes. Plant Molec. Biol. 13: 731–733.

CHUPEAU M. C., BELLINI C., GUERCHE P., MAISONNEUVE B., VASTRA G., CHUPEAU Y. (1989) Transgenic plants of lettuce (*Lacuca sativa*) obtained through electroporation of protoplasts. Bio/technology 7: 503–508.

CLARK R. B. Physiology of cereals for mineral nutrient uptake, use, and efficiency, in "Crops as enhancer of nutrient use" Baligar V. C. and Duncan R. R. Eds Academic press, San Diego, London (1990) pp 131–210.

CRAWFORD N. AND DAVIS R. W. Molecular analysis of nitrate regulation of nitrate reductase in squash and Arabidopsis, in "Molecular and genetic aspects of nitrate assimilation" Wray J. and Kinghorn J. R. Eds Oxford Science Publications, Oxford, New York, Tokyo (1989) pp 328–337.

CRAWFORD, N., SMITH, M., BELLISSIMO, AND DAVIS, R. W. (1988) Sequence and nitrate regulation of the *Arabidopsis thaliana* mRNA encoding nitrate reductase, a metalloflavo-protein with three functional domains. Proc. Natl. Acad. Sci. USA 85: 5006–5010.

CURIE C., LIBOZ T., BARDET C., GANDER E., MEDALE C., AXELOS M., LESCURE B. (1991) Cis and trans-acting elements involved in the activation of *Arabidopsis thaliana* A1 gene encoding the translation elongation factor EF-la Nucleic Acid Res. 19: 1305–1310.

DANIEL-VEDELE, F. DORBE, M. F., CABOCHE, M., AND ROUZE, P. (1989) Cloning and analysis of the nitrate reductase gene from tomato: a comparison of nitrate reductase protein sequences in higher plants. Gene 85: 371–380.

HOEKEMA A., HIRSCH P. R., HOOYKAAS P. J. J. and SCHILPEROORT R. A.—1983—A binary plant vector strategy based on separation of vir- and T-region of the *Agrobacterium tumefaciens* Ti-plasmid. Nature, 303, 179–180.

HOFF, T., STUMMANN, B. M., AND HENNINGSSEN, K. W. (1991) Cloning and expression of a gene encoding a root specific nitrate reductase in bean (*Phaseolus vulgaris*). Physiol. Plant; 82: 197–204.

HORSH R. B. AND KLEE H. J. (1986) Rapid assay of foreign gene expression in leaf discs transformed by *Agrobacterium tumefaciens* Proc. Natl. Acad. Sci. USA 83: 4428–4432.

KAY R., CHAN A., DALY M., McPHERSON J. (1987) Duplication of CaMV 35S promoter sequences creates a strong enhancer for plant genes Science 236: 1299–1302.

KLEINHOFS, A., WARNER R. L., HAMAT, H. B., JURIDEK, M., HUANG, C., AND SCHNORR, K. (1988) Molecular genetics of barley and rice nitrate reductases. Curr. Topics Plant Biochem. Physiol. 7: 35–42.

McCABE D. E., SWAIN W., MARTINELLI B., CHRISTOU P. (1988) Stable transformation of soybean (*Glycine max*) by prticle acceleration. Bio/technology 6: 923–927.

NEUHAUS G., SPANGENBERG G., MITTELSTEIN SCHIED O., SCHWEIGER H. G. (1987) Transgenic rapeseed plants obtained by the microinjection of NDNA into microspore-derived embrioids. Theor. Appl. Genet. 75: 30–36.

OSTREM J. A. AND COLLINS G. B. (1983) Genetic variation for nitrate concentration in *Nicotiana tabacum* L. J. Heredity 74: 431–434.

ROCHA-SOSA M., SONNEWALD U., FROMMER W. STRATMAN M., SCHELL J., WILLMITYZER L. (1989) Both develomental and metabolic signals activate the promoter of a class I patatin gene. EMBO J. 8: 23–29.

SAUX C., LEMOINE Y., MARION-POLL A., VALADIER M. H., DENG M., MOROT-GAUDRY J. F. (1987) Consequences of absence of nitrate reductase activity on photosynthesis in *Nicotiana plumbaginifolia* plants. Plant. Physiol. 84: 67–72.

STOCHER R. J., SCHILLITO R., SAUL M., PASKOWSKI J., POTRYKUS I. (1986) Co-transformation of unlinked foreign genes into plants by direct gene transfer. Bio/technology 4: 1093–1096.

THOMAS S. P. (1980) Hybridization of denatured RNA and small DNA fragments transferred to nitrocellulose. Proc. Natl. Acad. Sci. USA 67: 442–447.

THOMSON W. F. AND WHITE M. J. (1991) Physiological and molecular studies of light-regulated nuclear genes in higher plants. Ann. Rev. Plant Physiol. Plant Mol. Biol. 2: 423–466.

VAUCHERET, H., VINCENTZ, M., KRONENBERGER, J., CABOCHE, M., AND ROUZE, P. (1989) Molecular cloning and characterization of the two homeologous genes coding for nitrate reductase in tobacco. Mol. Gen. Genet. 16: 10–15.

VINCENTZ M. and CABOCHE M.—1991—Constitutive expression of nitrate reductase allows normal growth and development of *Nicotiana plumbaginifolia* plants. EMBO J., 10, 1027–1035.

WARNER R. L. AND HUFFAKER R. C. (1989) Nitrate transport is independent of NADH and NADPH nitrate reductases in barley seedlings. Plant Physiol. 91: 947–953.

WRAY—1986—The molecular genetics of higher plant nitrate assimilation—In, A genetic approach to Plant Biochemistry, A. D. Blonstein and P. J. King, eds (Springer, N.Y.), pp. 101–157.

ZAMBRYSKI P., JOOS H., GENETELLO C., LEEMANS J., VAN MONTAGU M., SCHELL J. (1983) Ti plasmid vector for the introduction of DNA into plant cells without alteration of their normal regeneration capacity EMBO J 2: 2143–2150.

We claim:

1. Method for enhancing the earliness of a plant and/or lowering the content of nitrates stored in the plant, comprising introducing into the genome of the plant under conditions permitting its expression, a foreign gene coding for nitrate reductase to induce an over expression of nitrate reductase in the plant.

2. A method according to claim 1 wherein the gene coding for nitrate reductase originates from cDNA of dicotyledonous plants coding for nitrate reductase.

3. A method according to claim 2, further comprising infecting explants with an *Agrobacterium tumefaciens* or *Agrobacterium rhizogenes* strain transformed with a plasmid into which is inserted said foreign gene coding for nitrate reductase, placed under the control of elements providing for expression of said gene.

4. A method according to claim 3 wherein the foreign gene coding for nitrate reductase is inserted into a plasmid derived from the Ti or Ri plasmid.

5. A method according to claim 4 further comprising placing the foreign gene coding for nitrate reductase under the control of a heterologous promoter which is functional in the transformed plant.

6. A method according to claim 5 wherein the foreign gene coding for nitrate reductase is derived from the Nia 2 gene for nitrate reductase of tobacco.

7. A method according to claim 5 further comprising placing the foreign gene coding for nitrate reductase under the control of the 35S RNA promoter of CaMV.

8. A method according to claim 5 wherein the foreign gene coding for nitrate reductase is inserted into plasmid pBin 19.

9. Plant displaying enhanced earliness, obtained by the method of claim 1.

10. Plant having a reduced content of stored nitrates, obtained by the method of claim 1.

11. Plant according to claim 9 selected from the group consisting of tobacco, lettuce, spinach, carrot and cabbage.

12. Plant according to claim 10 selected from the group consisting of tobacco, lettuce, spinach, carrot and cabbage.

* * * * *